(12) United States Patent
Leube et al.

(10) Patent No.: US 12,016,627 B2
(45) Date of Patent: Jun. 25, 2024

(54) METHOD AND DEVICE FOR DETERMINING A REFRACTIVE ERROR

(71) Applicant: Carl Zeiss Vision International GmbH, Aalen (DE)

(72) Inventors: Alexander Leube, Aalen (DE); Torsten Strasser, Tübingen (DE); Arne Ohlendorf, Tübingen (DE); Eberhart Zrenner, Tübingen (DE); Siegfried Wahl, Donzdorf (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 18/398,286

(22) Filed: Dec. 28, 2023

(65) Prior Publication Data

US 2024/0122467 A1 Apr. 18, 2024

Related U.S. Application Data

(63) Continuation of application No. 18/049,307, filed on Oct. 25, 2022, which is a continuation of application No. PCT/EP2021/061148, filed on Apr. 28, 2021.

(30) Foreign Application Priority Data

Apr. 29, 2020 (EP) .................................. 20172146

(51) Int. Cl.
*A61B 3/032* (2006.01)
*A61B 3/00* (2006.01)
(Continued)

(52) U.S. Cl.
CPC ............ *A61B 3/032* (2013.01); *A61B 3/0033* (2013.01); *A61B 3/0041* (2013.01); *A61B 3/103* (2013.01);
(Continued)

(58) Field of Classification Search
CPC ................................................ A61B 3/00–185
See application file for complete search history.

(56) References Cited

U.S. PATENT DOCUMENTS

| | | | |
|---|---|---|---|
| 2012/0019779 | A1 | 1/2012 | Legerton et al. |
| 2013/0176534 | A1 | 7/2013 | Frankfort et al. |

(Continued)

FOREIGN PATENT DOCUMENTS

| | | | |
|---|---|---|---|
| EP | 3329837 | A1 | 6/2018 |
| EP | 3730036 | A1 | 10/2020 |

OTHER PUBLICATIONS

Thibos et al., "Power Vectors: An Application of Fourier Analysis to the Description and Statistical Analysis of Refractive Error", Optometry and Vision Science 74 (6), pp. 367 to 375, 1997.

(Continued)

*Primary Examiner* — David J. McCrosky
(74) *Attorney, Agent, or Firm* — Tautz & Schuhmacher LLC; Georg Hasselmann

(57) ABSTRACT

A method, a device, and a computer program product for determining a refractive error of an eye of a user are disclosed, as well as a method for producing a spectacle lens. The method for determining includes: displaying an image with a spatial modulation to the user; optionally, recording a reaction of the user to a variation of the spatial modulation over time; detecting a point in time at which a perception threshold of the user is reached; and determining the refractive error of the user from the spatial modulation, wherein the image contains a source image with several picture elements, wherein values for an image parameter are assigned to the picture elements, and wherein the spatial modulation is generated such that the values of the image parameter determine the values of a modulation parameter of the spatial modulation in the image.

27 Claims, 2 Drawing Sheets

(51) Int. Cl.
  *A61B 3/103* (2006.01)
  *G02C 7/02* (2006.01)
  *G06T 3/40* (2024.01)
  *G06T 3/60* (2024.01)

(52) U.S. Cl.
  CPC .............. *G02C 7/027* (2013.01); *G06T 3/40* (2013.01); *G06T 3/60* (2013.01)

(56) References Cited

U.S. PATENT DOCUMENTS

| | | |
|---|---|---|
| 2020/0008667 A1 | 1/2020 | Raviv et al. |
| 2021/0312613 A1 | 10/2021 | Rosenberg Maffia et al. |
| 2022/0039646 A1 | 2/2022 | Ohlendorf et al. |

OTHER PUBLICATIONS

Industrial Norm "Ophthalmic optics—Spectacle lenses—Vocabulary (ISO 13666:2012)," German and English version EN ISO 13666:2012, Oct. 2013.

Dehnert et al., "Subjective visual acuity with simulated defocus," Ophthalmic and Physiological Optics, vol. 31, Issue 6, Abstract, Jul. 14, 2011.

Strasser et al., "They Can Disappear—Can the panda illusion be used to test visual acuity?", ARVO Annual Meeting Abstract, Investigative Ophthalmology & Visual Science (IOVS) 58 (8), Jun. 2017.

Strasser et al., "Can you see the panda? Visual acuity assessment using the pandacuity test in children—preliminary results", ARVO Annual Meeting Abstract, IOVS 59 (9), Jul. 2018.

Strasburger et al., "Blur unblurred—a mini tutorial," i-Perception, vol. 9(2), pp. 1 to 15, 2018.

Industrial Norm "Ophthalmic optics—Spectacle lenses—Vocabulary (ISO 13666:2019)", English version EN ISO 13666:2019, Dec. 2019.

Strasser et al., "The perception threshold of the panda illusion, a particular form of 2D pulse-width-modulated halftone, correlates with visual acuity," Scientific Reports, vol. 10, Issue 1, 2020.

International Search Report and Written Opinion issued in PCT/EP2021/061148, to which this application claims priority, mailed Jul. 14, 2021.

International Preliminary Report on Patentability issued in PCT/EP2021/061148, to which this application claims priority, mailed Sep. 12, 2022.

Office Action by the Australian Patent Office (IP Australia) issued in AU 2021263957, which is a counterpart hereof, mailed on Nov. 16, 2022.

METHOD AND DEVICE FOR DETERMINING A REFRACTIVE ERROR

CROSS REFERENCE TO RELATED APPLICATIONS

This application is a continuation application of U.S. patent application Ser. No. 18/049,307, filed Oct. 25, 2022, which is a continuation application of international patent application PCT/EP2021/061148, filed Apr. 28, 2021, designating the United States and claiming priority from European patent application EP 20 172 146.1, filed Apr. 29, 2020, and the entire content of all applications is incorporated herein by reference.

TECHNICAL FIELD

The present disclosure relates to a method, a device, and a computer program product for determining a refractive error of at least one eye of a user, as well as to a related method for producing at least one spectacle lens for the at least one eye of the user.

BACKGROUND

Various methods, devices and computer program products for determining the refractive error of at least one eye of a user are known. Herein, the terms "refraction" or "refractive" refer to a bending of incident light entering the interior of the eye via the pupil. For determining a value for the refractive error of the eye a subjective approach is, typically, applied in which an optometrist or an ophthalmologist performs an interactive test with the user. Herein, symbols, in particular in form of numbers, letters, or logos, are provided on a board, such as a cardboard, in a booklet, or on a screen to the user who, consecutively, views through a plurality of optical lenses having different optical refraction until a spectacle lens is determined by which the user can best recognize the smallest symbols. Thereafter, this procedure is repeated with measuring glasses having a different cylindrical refraction. Alternatively or in addition, an objective approach can be used, in which the optometrist or the ophthalmologist uses an autorefractive device. In this manner, values for the spherical and the cylindrical proportions of the refractive error can be obtained independently of the actually applied approach.

However, the known approaches require both the presence of an optometrist or an ophthalmologist and a satisfactory communication between the optometrist or the ophthalmologist, on one hand, and the user, on the other hand, which is not always possible, in particular due to a young age or an older age of the user, or as a consequence of language differences between the user and the optometrist or the ophthalmologist or a disease, respectively. Further, as indicated above, the sophisticated apparatus which is, typically, used for the objective approach requires high investment, maintenance and operation expenses that cannot be afforded at every place, viewed on a global scale.

US 2012/0019779 A1 discloses a method of measuring retinal or visual pathway function comprising stimulating optokinetic nystagmus by presenting a visual stimulus to a patient; modifying a first parameter of the visual stimulus; modifying a second parameter of the visual stimulus; and using the modified visual stimulus to determine a threshold stimulus for optokinetic nystagmus; wherein the first and second parameters are selected from a group of parameters comprising a pattern for the visual stimulus, a width of the visual stimulus, a distance between the visual stimulus and the patient, a spatial frequency of the visual stimulus, a rate of change or temporal frequency of the test face of the visual stimulus, and a contrast between elements of the visual stimulus.

US 2013/0176534 A1 discloses a method for adaptively determining a model of visual performance of a test subject comprising the step of exposing a test subject to a plurality of trials. Each trial comprises the steps of identifying the stimulus pattern to test, generating a stimulus pattern on a display, determining whether the stimulus pattern generated an OKR, updating the model to incorporate the OKR results, and determining whether the updated model is acceptable. The trials can be iteratively repeated until the model for visual performance is acceptable.

EP 3 329 837 A1 discloses a method for displaying optotype representations to assess at least one of a refractive error or a contrast sensitivity of the visual system of a test person which comprises providing a plurality of optotypes, comprising a base pattern and one or more modulated versions of said base pattern, wherein a contour of said base pattern is defined by a closed curve and said one or more modulated versions of said base pattern have contours being defined by modulated versions of said closed curve; providing a test system for measuring at least one of a refractive error or a contrast sensitivity of the visual system of a test person; and displaying representations of said plurality of optotypes via a display device of said test system. Further, an optotype representation and its use in a test of visual system, a test system and a computer program product are provided.

EP 3 730 036 A1 discloses a method, a device and a computer program for determining a refractive error of an eye of a user as well as a method for producing a spectacle lens for the eye of the user. Herein the method comprises presenting a symbol on a screen, wherein a parameter of the symbol displayed on the screen is changed; recording a reaction of the user depending on the symbol displayed on the screen; detecting a point in time at which a perception threshold of the user is indicated by a reaction of the user to the symbol displayed on the screen; and determining a value for the refractive error of the eye of the user from the parameter at the point in time, wherein the symbol displayed on the screen is a periodic pattern, wherein the parameter of the symbol displayed on the screen comprises a spatial frequency, wherein the value for the refractive error is determined from the spatial frequency at the point in time.

Torsten Strasser, Hana Langrová, Laura Kuehlewein, Annette Werner, Anne Kurtenbach and Eberhart Zrenner, *THEY CAN DISAPPEAR—Can the panda illusion be used to test visual acuity?*, ARVO Annual Meeting Abstract, Investigative Ophthalmology & Visual Science (IOVS) 58(8), June 2017, describe that the artist Ilja Klemencov revealed the artwork "They can disappear" in 2016, pointing out the danger of extinction of the panda bear. The illustration shows the WWF logo, a panda, hidden behind black-and-white zigzagged lines. Many people struggle to spot the bear at a first glance. However, stepping back or taking off the glasses unveils the panda. The authors found a significant correlation between a limiting spatial frequency and visual acuity of a user. However, the variability of a predicted visual acuity is rather wide. The illusion may not be completely explained by the visual acuity alone. Other contributing factors may be the point spread function or visual crowding. Nevertheless, the counterintuitive application of this illusion and the simplicity of the test may render it useful for estimating the visual acuity.

Torsten Strasser, Bettina Spieth, Eberhart Zrenner, Dorothea Besch, and Carina Kelbsch, *Can you see the panda? Visual acuity assessment using the pandacuity test in children—preliminary results*, ARVO Annual Meeting Abstract, IOVS 59(9), July 2018, indicate that visual acuity testing in preschool or developmentally delayed children can be challenging and is highly reliant on the child's compliance. Typically used acuity charts with simple optotypes could bore the child, making it difficult to distinguish between non-compliance and decreased visual acuity. The authors developed a pandacuity test using a flip book with a panda illusion-like image with decreasing visual acuity score on each page created based on the linear relationship as described in Torsten Strasser, IOVS 58(8), see above. They found that the pandacuity test is rapid, simple, and well-accepted, making it a suitable addition to conventional acuity testing for clinical assessment of visual acuity in children.

SUMMARY

In particular with respect to the disclosure of EP 3 730 036 A1, it is therefore an objective of the present disclosure to provide a method, a device, and a computer program product for determining a refractive error of at least one eye of a user as well as a related method for producing at least one spectacle lens for the at least one eye of the user, which at least partially overcome the above-mentioned problems of the related art.

It is a particular objective of the present disclosure to be able to determine values for the spherical and the cylindrical proportions of the refractive error by applying a simple and easy-to-use approach. Thereby, it is desirable to be able to determine the desired values without requiring an optometrist, an ophthalmologist, a set of measuring glasses and/or a sophisticated apparatus, such as an autorefractive device, being designated for this purpose. In particular, it is desirable to determine the refractive error of at least one eye of the user in a fashion which can be applied on a global scale to all kinds of users, including children, elderly or handicapped people, whereby difficulties with communication or compliance can be avoided as far as possible.

This problem is solved by a method, a device, and a computer program product for determining a refractive error of at least one eye of a user as well as a related method for producing at least one spectacle lens for the at least one eye of the user with a source image having a plurality of picture elements. Exemplary embodiments, which might be realized in an isolated fashion or in any arbitrary combination, are discussed in detail below.

As used in the following, the terms "have," "comprise," or "include" or any arbitrary grammatical variations thereof are used in a non-exclusive way. Thus, these terms may refer to both a situation in which, besides the feature introduced by these terms, no further features are present in the entity described in this context and to a situation in which one or more further features are present. As an example, the expressions "A has B," "A comprises B," and "A includes B" may both refer to a situation in which, besides B, no other element is present in A (i.e., a situation in which A solely and exclusively consists of B) and to a situation in which, besides B, one or more further elements are present in entity A, such as element C, elements C and D, or even further elements.

Further, as used in the following, the terms "preferably," "more preferably," "particularly," "more particularly," or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an embodiment of the disclosure" or similar expressions are intended to be optional features, without any restriction regarding alternative embodiments of the disclosure, without any restrictions regarding the scope of the disclosure and without any restriction regarding the possibility of combining the features introduced in this way with other features of the disclosure.

In a first aspect, the present disclosure relates to a method for determining at least one refractive error of at least one eye of a user. As already indicated above, the terms "refraction" or "refractive" refer to a bending of incident light entering the interior of the eye via the pupil. Instead of the term "user," a different term, such as "subject," "person," "test person" or "wearer of eye glasses," may also be applicable. Herein, the method can be used for individually determining the refractive error of each eye of a user in a consecutive or in a simultaneous fashion.

The method according to the present disclosure comprises the following steps a), c) and d), preferably in the given order:
  a) displaying at least one image to a user, wherein the at least one image comprises at least one spatial modulation;
  b) detecting a point in time at which a perception threshold of the user is indicated by a reaction of the user; and
  c) determining a value for the at least one refractive error of the at least one eye of the user from the at least one spatial modulation in the at least one image at the point in time,
    wherein the at least one image comprises a source image having a plurality of picture elements, wherein values for at least one image parameter are assigned to the plurality of picture elements, wherein the at least one spatial modulation in the at least one image is generated in a manner that the values of the at least one image parameter of the plurality of picture elements determine the values of at least one modulation parameter of the at least one spatial modulation in the at least one image.

Alternatively, the method according to the present disclosure comprises the following steps a) to d):
  a) displaying at least one image to a user, wherein the at least one image comprises at least one spatial modulation;
  b) recording a reaction of the user to at least one variation of the at least one spatial modulation over time;
  c) detecting a point in time at which a perception threshold of the user is indicated by a reaction of the user; and
  d) determining a value for the at least one refractive error of the at least one eye of the user from the at least one spatial modulation in the at least one image at the point in time,
    wherein the at least one image comprises a source image having a plurality of picture elements, wherein values for at least one image parameter are assigned to the plurality of picture elements, wherein the at least one spatial modulation in the at least one image is generated in a manner that the values of the at least one image parameter of the plurality of picture elements determine the values of at least one modulation parameter of the at least one spatial modulation in the at least one image.

The point in time at which a perception threshold of the user is indicated by a reaction of the user according to the above-mentioned step c) may be detected by an assistant or a third person or a measuring device. The reaction of the user preferably may be evoked by at least one variation of the at least one spatial modulation over time. The reaction of the user may be for example a physiological reaction, such as for example a pupil reaction or a verbal reaction. The reaction of the user may be detected for example by an electrophysiological monitoring method, such as electroencephalography (EEG), by using a measuring device configured to monitor the behavior of the user, such as a video camera, wherein the reaction of the user can be observed by displaying the video or, alternatively or in addition, by image processing or by using a measuring device configured to monitor eye movements of the user. The behavior of the user or the eye movements may indicate the perception threshold of the user as described below. Alternatively, the physiological reaction of the user may be an involuntary reaction, especially caused by a reflex.

In general, the method according to the present disclosure can be performed in a manual fashion in which an assistant supporting the user may display the at least one image to the user and may vary the spatial modulation in the at least one image over time as described below in more detail, wherein the at least one image may be provided in printed form, in particular on a board, such as a cardboard, or in a booklet, wherein the source image and the corresponding spatial modulation thereof may have been generated beforehand by using a device configured for this purpose, such as a printer, wherein a value that is related to the at least one spatial modulation in the at least one image may, additionally, be printed on the board, such as the cardboard, or in the booklet, preferably on a margin thereof, thus, avoiding a disturbance of the at least one image.

However, in a particular embodiment, the method according to the present disclosure may be a computer-implemented method. As generally used, the term "computer-implemented method" refers to a method which involves a programmable apparatus, in particular an evaluation unit, specifically a computer, a computer network, or a readable medium carrying a computer program, whereby at least one of the features of the method is performed by using at least one computer program. Herein, the computer program code may be provided on a data storage medium or a separate device such as an optical storage medium, e.g., on a compact disc, directly on a computer or a data processing unit, in particular a mobile communication device, specifically a smartphone or a tablet, or via a network, such as an in-house network or the internet. The present method can, thus, being performed on a programmable apparatus which is configured for this purpose, such as by providing a particular computer program.

The present method for determining at least one refractive error of at least one eye of a user can, preferably, be used in a method for producing at least one spectacle lens for the at least one eye of the user as described below in more detail. Based on standard ISO 13666:2019, also referred to herein as the "standard," Section 3.5.2, the term "spectacle lens" relates to an optical lens which is used within the framework of the present disclosure for determining and/or correcting a defective vision of a user, wherein the optical lens is carried in front of the eye of the user, thereby avoiding a direct contact with the eye. Further, the term "glasses" refers to an arbitrary element which comprises two individual spectacle lenses and a spectacle frame, wherein each spectacle lens is prepared for being received by the spectacle frame selected by the user.

In particular, the determining of the at least one refractive error of at least one eye of a user can comprise determining a spherocylindrical lens which is, in general, used as a spectacle lens to correct the at least one refractive error of the at least one eye of the user. For describing the spherocylindrical lens, various approaches are possible. As defined in the standard, Section 3.6.6, the term "spherocylindrical lens" refers to a spectacle lens having a spherical surface and a cylindrical surface. Further, the spherocylindrical lens is defined, according to Section 3.13.1, as a spectacle lens which combines a paraxial, parallel beam of light in two individual, mutually perpendicular focal lines, whereby the spectacle lens has an apex refractive power only in the two main sections. Further, the term "apex refractive power" is, according to Section 3.10.7, defined as a reciprocal value of the width of the paraxial section. As further defined in Section 3.13.2, the term "main section" relates to one of two perpendicular meridians of the spectacle lens having an astigmatic effect being parallel to the two focal lines. Herein, the term "astigmatic effect" corresponds to an "astigmatic difference" which is defined in Section 3.13.6 as a difference between the value of the apex refractive power in the second main section and the value of the apex refractive power in the first main section. Further, the "cylindrical power" refers, according to Section 3.13.7, to an algebraic difference between the refractive values of the main sections, wherein the refractive value of a particular main section being used as a reference is subtracted from the refractive value of the other main section, while the "cylinder axis" indicates according to Section 3.13.8 the direction of the main section of the spectacle lens whose apex refractive index is used as the reference.

As an alternative, L. N. Thibos, W. Wheeler and D. Homer (1997), Power Vectors: An Application of Fourier Analysis to the Description and Statistical Analysis of Refractive Error, Optometry and Vision Science 74 (6), S. 367-375, propose to approach the description of a spherocylindrical lens from a viewpoint of Fourier analysis of a power profile. They show that the familiar sine-squared law leads naturally to a Fourier series representation with exactly three Fourier coefficients, representing natural parameters of a thin lens. Herein, a constant term corresponds to a mean spherical equivalent (MSE) power, whereas amplitude and phase of the harmonic correspond to the power and axis of a Jackson cross-cylinder (JCC) lens, respectively. Expressing the Fourier series in rectangular form leads to the representation of an arbitrary spherocylindrical lens as sum of a spherical lens and two cross-cylinders, one at axis 0° and the other at axis 45°. The power of these three component lenses may be interpreted as (x, y, z) coordinates of a vector representation of the power profile. The power vector representation of a spherocylindrical lens can be used for numerical and graphical analysis of optometric data for problems involving lens combinations, comparison of different lenses, and statistical distribution of refractive errors.

According to step a), at least one image is displayed to a user, wherein the at least one image comprises at least one spatial modulation. As generally used, the term "image" refers to a two-dimensional representation of at least one of an object or an abstract idea, such as a number, a letter, or a logo, denoted herein by the term "symbol," which can be modified within the image in an arbitrary fashion, wherein the displayed image or a change thereof over time may act as a stimulus to at least one eye or to the eyes of the user as described below in more detail. With particular respect to the present disclosure, the at least one image, thus, comprises a source image, preferably selected from a recording or a drawing of an object, preferably of an object that can easily be recognized and denominated by the user, including a child, an elderly or a handicapped person, wherein the at least one spatial modulation is generated by modifying the source image in a predefined manner. For this purpose, the source image can, in principle, be an arbitrary picture as long as it illustrates an object that is easily recognizable and denotable by the user, preferably, selected from a simple logo, an animal, a toy, a natural object such as a house or a fruit.

According to the present disclosure, the at least one image, thus, comprises a source image, wherein the source image has a plurality of picture elements. As generally used, the terms "picture element" or "pixel" refer to a portion of an image which can be individually addressed, such as in a representation of the image on a board, such as cardboard, in a booklet, or on a screen. Herein, a value for at least one image parameter is assigned to each picture element, wherein, apart from a completely uniform image, the value for the at least one image parameter can vary between different picture elements, in particular between adjacent picture elements. As used herein, the term "image parameter" refers to a quantity which is visually recognizable by a user which is associated with a picture element, wherein the quantity can, preferably, be selected from at least one of: an intensity of the picture element, a grayscale of the picture element, a color of the picture element, a polarization of the picture element, a temporal variation of the picture element. However, other kinds of image parameters may also be feasible. As a result of this assignment, the value of the at least one image parameter is designated to describe at least one of an intensity of the picture element, a grayscale of the picture element, a color of the picture element, a polarization of the picture element, or a temporal variation of the picture element.

Further according to the present disclosure, the spatial modulation in the at least one image is generated by modulating the picture elements in the source image, whereby the at least one image is created. As used herein, the terms "modulating" or "modulation" relate to a modification of the source image comprising a modifying of the values of the at least one image parameter of the picture elements within the source image in a repetitive manner Thus, the terms "spatial modulation" or "spatially modulating" relate to a modulation of the image in space which can be maintained constant over time. As a result, a spatial frequency can be assigned to the spatial modulation, wherein the term "spatial frequency" refers to a reciprocal value of a spatial distance which reflects a spatial period of repetition of a pattern within the image, wherein the term "spatial period" which corresponds to a reciprocal value of the special frequency may also be replaced by the term "cycle." Thus, a value of a spatial frequency can be specified by using a number accompanied by a unit of l/m or, alternatively, of "per degree." However, absolute values of the spatial period and the spatial frequency depend on a distance between the image comprising the spatial modulation and the user viewing the spatial modulation. Consequently, altering this distance results in an alteration in which the image appears to at least one eye or to the eyes of the user, whereby the absolute values of both the spatial period and the spatial frequency are modified. By way of example, the at least one image may comprise a source image which can be a schematic drawing of a symbol, wherein the spatial modulation in the at least one image can be generated by superimposing stripes onto the source image, wherein a distance or an angular range between adjacent stripes indicate the spatial frequency.

In accordance with the present disclosure, the spatial modulation in the at least one image is generated by modulating the picture elements of the source image in a particular fashion, namely in a manner that the value of the at least one image parameter of the picture element determines the value of at least one modulation parameter of the at least one spatial modulation of the picture element. As used herein, the term "modulation parameter" refers to a characteristic feature of the modulation which, apart from the spatial frequency of the modulation, introduces a further type of modulation in a manner that each spatial period as defined by the spatial frequency can be shaped in an individual fashion without influencing the value of the spatial frequency at all. The spatial frequency which remains unaffected by the further type of modulation, therefore, corresponds to a "carrier frequency" of the modulation since it is configured to be superimposed by the at least one further type of modulation. Herein, a so-denoted "duty cycle" refers to a portion of a particular spatial period during which the modulation is applied, wherein a value of the duty cycle may vary between adjacent spatial periods, whereby the spatial frequency is left unaffected.

In a particularly preferred embodiment of the present disclosure, the modulation type of the at least one spatial modulation can be selected from at least one of: a pulse width modulation, an amplitude modulation, a frequency modulation. As generally used, the term "pulse width modulation" refers to a type of modulation which comprises a duty cycle as defined above as the at least one modulation parameter. As described below in more detail, a value for the duty cycle within a spatial period is determined in pulse width modulation based on the value of the at least one image parameter of the corresponding picture element. By way of example, the duty cycle within a particular spatial period can assume a value of "HIGH" if the color of the corresponding picture element comprised by that particular spatial period may be "black," and a value of "LOW" if the color of the corresponding picture element may be "white." However, various further examples are conceivable.

As further generally used, the term "amplitude modulation" refers to a type of modulation in which a value for the amplitude of the modulation within a spatial period is determined by using the value of the at least one image parameter of the corresponding picture element. By way of example, the amplitude within a particular spatial period can assume a value of "HIGH" if the grayscale of the corresponding picture element comprised by the spatial period may exhibit a low intensity, and a value of "LOW" if the grayscale of the corresponding picture element may exhibit a high intensity. Again, the carrier frequency of the amplitude modulation remains unaffected. However, various further examples are possible.

As further generally used, the term "frequency modulation" refers to a type of modulation in which a value for a superimposed further frequency of the modulation within the spatial period is determined by considering the value of the at least one image parameter of a corresponding picture element. By way of example, the superimposed further frequency within a particular spatial period can assume a value of "HIGH" if the relative intensity of the corresponding picture element located within the spatial period may be "HIGH" and a value of "LOW" if the relative intensity of the corresponding picture element located within the spatial period may be "LOW." Also here, the carrier frequency of the modulation remains unaffected by this type of modulation. However, various further examples are feasible.

In a particular embodiment, a phase of the at least one carrier frequency can, however, additionally be modulated, in particular in a sinusoidal fashion, thereby generating a characteristic zig-zag pattern in the image. For further details, reference can be made to the description of the embodiments as presented below in more details.

According to step b), a reaction of the user to at least one variation of the at least one spatial modulation in the at least one image can be recorded over time. Herein, the at least one spatial modulation in the image can be varied over time in at least one fashion, preferably, selected from varying at least one spatial frequency of the at least one spatial modulation;
varying a distance between the at least one image and the at least one eye of the user;
rotating the at least one image in a plane perpendicular with respect to a direction of view of the user.

Consequently, the at least one spatial modulation can be varied by using one or more of embodiments (i) to (iii).

Herein, at least one variation of the at least one spatial frequency of the spatial modulation according to embodiment (i) may be performed in a manual fashion by displaying a different board, such as a cardboard, or a different page of a booklet illustrating a different image showing a different spatial frequency of the spatial modulation to the user, wherein the different images showing the different spatial frequencies may be presented in a predetermined order, such as consecutive cardboards or subsequent pages in a booklet. Alternatively, the variation of the at least one spatial frequency of the spatial modulation according to embodiment (i) can be achieved by displaying a different image on a screen showing the desired different spatial frequencies of the spatial modulation to the user, wherein the different images showing the different spatial frequencies may have been generated by using a data processing unit.

Further, the variation of the distance between the at least one image and the at least one eye of the user according to embodiment (ii) may be performed in a manual fashion by altering a position of the cardboard illustrating the same at least one image but resulting in showing a different spatial frequency of the spatial modulation to the user by the altered distance between the at least one image and the at least one eye of the user. Alternatively, the variation of the distance between the image and the at least one eye of the user according to embodiment (ii) can be achieved by moving at least one of the screens and the user with respect to each other, thereby displaying the same at least one image on the screen, whereby a different spatial frequency of the spatial modulation is shown to the user. In this embodiment, a distance meter or at least one camera may, preferably, be employed, wherein the distance meter and the at least one camera is, respectively, configured to determine a distance between the at least one image and the at least one eye of the user. For further details concerning the determination of the distance between the at least one image and the at least one eye of the user, reference can be made to EP 3 730 036 A1.

Further, a rotation of the at least one image within a plane perpendicular to a direction of view of the user according to embodiment (iii) may be performed in a manual fashion by turning the board, such as the cardboard, illustrating the same at least one image within a plane which is perpendicular with regard to the direction of view of the user, thereby maintaining the distance between the cardboard and the at least one eye of the user, which results in showing a different spatial frequency of the spatial modulation to the user due to the rotation of the at least one image within the plane perpendicular to the direction of view of the user. As an alternative, the rotation of the at least one image in a plane perpendicular to a direction of view of the user according to embodiment (iii) can be achieved by digitally rotating the at least one image on the screen without changing a further parameter of the image or of the screen. As a result, a different value for the spatial frequency of the spatial modulation is recognized by the user due to an alteration in which the at least one image appears of the user.

Independent of the manner of the variation of the spatial modulation in the at least one image, at least one of the images or the variation of the spatial modulation in the at least one image acts as a stimulus to at least one eye or to the eyes of the user, thereby initiating a response of the use, wherein the response of the user is, generally, referred to by the term "reaction." As generally used, the term "recording" relates to any kind of recognizing the reaction of the user, either by observing the behavior of the user or, alternatively or in addition, by monitoring a measurement signal, in particular an electronic signal, which can be provided by at least one of a measuring device or an input unit designated for this purpose. In particular, the measuring signal can be provided to an evaluation unit which is configured to detect the point in time at which a perception threshold of the at least one image for the user is indicated by the reaction of the user to the variation of the spatial modulation in the at least one image according to step c). In particular, the reaction of the user can be recorded simultaneously for both eyes or, alternatively or in addition, in a consecutive fashion. For the latter, one of the eyes of the user can, for example, be covered, in particular, initiated by a supervisor or a corresponding menu in the measuring device.

As already mentioned, the reaction of the user can be recorded by using an input unit, wherein the input unit configured to record a reaction of a user to a variation of a spatial modulation in at least one image over time. As generally used, the term "input unit" refers to a device which is configured to monitor an occurrence of an event by providing or interrupting a measurement signal at a point in time at which the event occurs. In particular, the input unit can be a keyboard, which may comprise at least one key to be pressed by the user in order to express the reaction. Herein, the keyboard may be at least one of a real keyboard or a virtual keyboard, such as comprised by a touchscreen. Alternatively or in addition, the input unit may comprise at least one microphone configured to receive a sound produced by the user to indicate the desired reaction.

As a further alternative or in addition, the reaction of the user can be recorded by using a measuring device, wherein the measuring device is configured to monitor the behavior of the user. In particular, a video camera can be used for recording a video of the user, wherein the reaction of the user can be observed by displaying the video or, alternatively or in addition, by image processing. As a further alternative or in addition, the measuring device can be configured to monitor eye movements of the user. As generally used, the term "eye movements" relates to a motion of one or both eyes of a user which can be recorded, in particular by employing an eye tracker, wherein the eye tracker is configured to record monocular track data or, preferably, binocular track data. Apart from spontaneous eye movements, the movement of the eyes of a user can be triggered by a stimulus which may be initiated here by the at least one image, or by the variation of the spatial modulation in the at least one image. Herein, the eye movements to be recorded may be selected from pursuit eye movements.

As generally used, the term "pursuit eye movements" refers to a movement of the eye initiated by a stimulus, wherein at least one eye follows, or the eyes follow the stimulus or a variation over time thereof, wherein the eye movements become random if the stimulus is not visible by the user. Therefore, the movement of the eye initiated by a stimulus may be used to record the reaction of the user.

As a further alternative, the reaction of the user according to step c) can be indicated by using a measuring device, wherein the measuring device is configured to monitor the behavior of the user. In particular, a video camera can be used for recording a video of the user, wherein the reaction of the user can be observed by displaying the video or, alternatively or in addition, by image processing. As a further alternative or in addition, the measuring device can be configured to monitor eye movements of the user. Apart from spontaneous eye movements, the movement of the eyes of a user can be triggered by a stimulus which is initiated here by the at least one image or the variation of the spatial modulation in the at least one image. Herein, the eye movements to be recorded may be selected from pursuit eye movements. For a definition of the terms "eye movements" and "pursuit eye movements," reference can be made to the description above. Therefore, the movement of the at least one eye initiated by a stimulus may be used as the indication of the point in time for the perception threshold of the user without requiring recording the reaction of the user to at least one variation of the at least one spatial modulation over time according to step b). Herein, the perception threshold of the user may, preferably, correspond to that point in time before the movement of the at least one eye becomes random.

According to step c), a point in time is detected at which a perception threshold of the user is indicated by a reaction of the user to the variation of the spatial modulation in the at least one image. As generally used, the term "perception threshold" is defined as a threshold above which the user is able to recognize a stimulus, in particular the variation of the spatial modulation in the at least one image. In particular, the term "perception threshold" comprises a first event in which the user is firstly be able to recognize the stimulus and a further event in which the user is just be able to recognize the stimulus before the stimulus vanishes. Accordingly, the point in time which is related to the first event or the further event can be detected, thereby indicating the perception threshold. In a first embodiment, the spatial modulation in the at least one image as displayed to the user according to the present disclosure can increase, thereby more and more impeding the recognizability of the stimulus by the user until the user is no longer be able to recognize the image at all. In a further embodiment, the spatial modulation in the at least one image as displayed to the user according to the present disclosure can decrease, thereby more and more facilitating the recognizability of the stimulus by the user until the user is firstly capable of recognizing the at least one image. In a further embodiment in which the at least one image parameter of the picture elements may be selected from at least one of an intensity, a grayscale, a color, a polarization, or a temporal variation of the picture elements, the perception threshold may, further, be selected from at least one of a contrast threshold, a color threshold, a polarization threshold, or a temporal threshold. In particular, the contrast threshold can be used when the at least one image parameter of the picture elements may comprise an intensity and/or a grayscale variation. Further, the color threshold can be used when the at least one image parameter of the picture elements may comprise a color variation. Further, the polarization threshold can be used when the at least one image parameter of the picture elements may comprise a polarization variation. Further, the temporal threshold can be used when the at least one image parameter of the picture elements may comprise a temporal variation.

Hereby, an evaluation unit can be used which is configured to detect the point in time at which a perception threshold of the at least one image for the user is indicated by the reaction of the user to the variation of the spatial modulation in the at least one image. However, as indicated above, an assistant may display the at least one image to the user and vary the spatial modulation in the at least one image over time in a manual fashion, wherein the at least one image may be provided in printed form on a board, such as a cardboard, wherein a value that is related to the at least one spatial modulation in the image may, additionally, be printed on the board, such as on a margin of the board, this, avoiding a disturbance of the at least one image. Herein, the particular at least one image or a particular feature related to the at least one image can, thus, be used for determining the desired value related to the at least one spatial modulation in the image.

According to step d), a value for at least one refractive error of the at least one eye of the user is determined from a value of at least one modulation parameter of the at least one spatial modulation in the at least one image at the point in time. As generally used, the term "determining" relates to a process of generating at least one representative result, such as a plurality of representative results, in particular by applying the method according to the present disclosure. Hereby, an evaluation unit can be used which is further configured to determine a value for at least one refractive error of the at least one eye of the user by using the point in time as detected during step c), wherein the point in time indicated a perception threshold of the at least one image for the user.

By detecting the point in time which corresponds to the perception threshold of the user according to step c), a value which corresponds to the spatial modulation in the at least one image at this point in time has, additionally, been determined. Independent of the manner of the variation of the spatial modulation in the at least one image as described above in more detail, the value of the spatial modulation in the at least one image at this point in a form as actually recognized by the user is determined in this fashion. Without rotating the at least one image according to embodiment (iii) as defined above, a refractive value of a single meridian of the spherocylindrical lens required to correct this part of the refractive error of the user can, thus, be determined. Rotating the at least one image, further allows determining the cylindrical power which refers, as defined above, to an algebraic difference between the refractive values of different meridians and the cylinder axis which indicates, as further defined above, the direction of the meridian of the spectacle lens or of the eye of the user where the surface curvature is at maximum. However, different definitions are possible.

In a particularly preferred embodiment of the present disclosure, a value for the refractive error of the at least one eye of the user can be determined by demodulating the at least one image which has, previously, been modulated during step a) by the type of modulation using the modulation parameter. Taking into account the value of the modulation parameter at the point in time, a demodulation of the at least one image can be considered as optically or analytically filtering the at least one image at the point in time. As a consequence thereof, a filter, in particular a filter function, can be used for the demodulation of the at least one image, whereby additional information related to the point in time can be derived. In particular, a frequency which is used for modulating source image can be considered as proportional to a power of the filter function which is, thus, proportional to a value for the refractive error of the user.

In a particularly preferred embodiment, the filter as used for the demodulation, typically, comprises a low pass filter function which is configured to remove high frequency portions from the at least one image. Herein, the filter may be capable of at least partially removing the spatial modulation from the at least one image, whereby the source image can be resumed to a large extent. Since the image comprises, as indicated above, a two-dimensional representation, a two-dimensional low pass filter is, preferably, applied for this purpose, wherein the two-dimensional low pass filter is, usually, denoted by one of the terms "Gauss filter" or "Sinc$^2$ filter." In order to be able to determine the cylindrical power and the cylinder axis as defined above, more than one filter can be used for different axes of the at least one image.

Alternatively or in addition, an optical filter can be used for the same purpose. As used herein, the term "optical filter" refers to a simulated spectacle lens having a predefined visual correction, such as indicated in ±diopters. In this particular embodiment, the optical filter can be is superimposed, in particular by the evaluation device, onto the at least one image in order to produce a corrected image. By consecutively superimposing different optical filters, wherein each optical filter corresponds to a simulated different spectacle lens having a different value for the visual correction, a corrected image can be obtained which may correspond to the desired value for the refractive error of the at least one eye of the user.

By way of example, a user is requested to view an image as provided on a screen according to step a) of the present method and to indicate according to step b) whether he or she is able to recognize the source image or not. Thereafter, the image is modified by using at least one filter which is capable of at least one of:

varying at least one spatial frequency of the spatial modulation according to embodiment (i) or (ii) as defined above or rotating the image in a plane perpendicular with respect to a direction of view of the user according to embodiment (iii) as further defined above.

As a consequence, the source image can, thus, be modulated with a different kind of spatial modulation over time in order to be able to detect spherical and meridional refractive errors of the user. Herein, a particular procedure for determining the at least one refractive error of the at least one eye of the user may be preferred which combines power and orientation of the filter with a power and orientation of the image. Preferably, at least one filter parameter which may be provided by applying the demodulation at the point in time can, subsequently, be correlated to a refractive error of the at least one eye of the user. In particular, a 2D parameter of the demodulation filter can provide information about an astigmatic component of the refractive error of the at least one eye of the user. However, a different kind of procedure may also be feasible.

In a further aspect, the present disclosure refers to a computer program product which comprises executable instructions for performing the method for determining a refractive error of at least one eye of a user according to the present disclosure. For this purpose, a computer program may comprise instructions provided by means of a computer program code which are capable of performing any or all of the steps of the methods as described elsewhere herein and, thus, to establish determining the refractive error of the at least one eye of a user when implemented on a computer or a data processing unit.

The computer program code may be provided on a data storage medium or a separate device such as an optical storage medium, e.g., on a compact disc, directly on a computer or a data processing unit, in particular a mobile communication device, specifically a smartphone or a tablet, or via a network, such as an in-house network or the internet.

For further details concerning the computer program product, reference may be made to the method according to the present disclosure as disclosed elsewhere herein.

In a further aspect, the present disclosure relates to a device for determining a refractive error of at least one eye of a user.

Herein, the device comprises at least:
a screen, wherein the screen unit is configured to display at least one image and at least one variation of at least one spatial modulation in the at least one image to a user;
an evaluation unit, wherein the evaluation unit is configured to detect a point in time at which a perception threshold of the user is indicated by a reaction of the user, and to determine a value for the at least one refractive error of the at least one eye of the user from the at least one spatial modulation in the at least one image at the point in time,
wherein the at least one image comprises a source image having a plurality of picture elements, wherein values for at least one image parameter are assigned to the plurality of picture elements, wherein the evaluation unit is further configured to generate the at least one spatial modulation in the at least one image in a manner that the values of the at least one image parameter of the plurality of picture elements determine the values of at least one modulation parameter of the at least one spatial modulation in the at least one image.

Herein, an input unit may, generally, not required since the perception threshold of the user can be indicated by a reaction of the user, wherein the reaction of the user may, preferably, be at least one physiological reaction. In particular, the at least one physiological reaction may be selected from at least one of the physiological reactions as indicated above. Alternatively, the device comprises at least:
a screen, wherein the screen unit is configured to display at least one image and at least one variation of at least one spatial modulation in the at least one image to a user;
an input unit, wherein the input unit is configured to record a reaction of the user to the at least one variation of the at least one spatial modulation in the image over time;
an evaluation unit, wherein the evaluation unit is configured to detect a point in time at which a perception threshold of the user is indicated by a reaction of the user, and to determine a value for the at least one refractive error of the at least one eye of the user from the at least one spatial modulation in the at least one image at the point in time,
wherein the at least one image comprises a source image having a plurality of picture elements, wherein values for at least one image parameter are assigned to the plurality of picture elements, wherein the evaluation unit is further configured to generate the at least one spatial modulation in the at least one image in a manner that the values of the at least one image parameter of the plurality of picture elements determine the values of at least one modulation parameter of the at least one spatial modulation in the at least one image.

In addition, each device according to the present disclosure may, further, comprise at least one of:

a processing unit, wherein the processing unit is configured to generate the at least one image and the variation of the spatial modulation in the at least one image;

a distance meter, wherein the distance meter is configured to determine a distance between the at least one image and the at least one eye of the user.

In a particularly preferred embodiment of the present disclosure, at least one of the screen, the processing unit and the evaluation unit may be integrated in a virtual reality headset. Alternatively, the screen, the evaluation unit, the processing unit and the distance meter can at least partially be comprised by a mobile communication device, specifically a smartphone or a tablet, which is in communication with the virtual reality headset. As generally used, the term "virtual reality headset" refers to a head-mounted device which is designated for providing virtual or augmented reality for the user who wears the virtual reality headset. In general, the virtual reality headset comprises a stereoscopic head-mounted display which may be capable of providing separate images for each eye; stereo sound; head motion tracking sensors, such as a gyroscope, an accelerometer, or a structured light system; and an eye tracking sensor. As further generally used, the term "mobile communication device" refers to a mobile communication device which comprises a mobile operating system being designated for facilitating a use of software, internet, and multimedia functionalities. In particular, the mobile communication device may comprise at least one camera and at least one sensor, in particular, selected from a gyroscope, an accelerometer, a proximity sensor, a magnetometer, or a barometer, and may support wireless communications protocols such as Wi-Fi or Bluetooth. Herein, the at least one camera and the processing unit of the mobile communication device may jointly be configured to determine a distance between the at least one image and the at least one eye of the user and can, thus, be employed as the distance meter.

In an alternative embodiment, the screen may be integrated in smart glasses whereas the evaluation unit can be comprised by a mobile communication device which is, preferably, in communication with the smart glasses. As generally used, the term "smart glasses" refers to glasses which are wearable by a user and which are designed for superimposing information onto a field of view of the user. Further, the smart glasses may be designated for changing optical properties when worn by the user. For these purposes, embedded wireless glasses with a transparent heads-up display or an augmented reality (AR) overlay may be used which, on one hand, allow a usual visual reception by the user and, on the other hand, are designed for projecting digital images provided by integrated applications.

Alternatively or in addition, further embodiments with respect to the device according to the present disclosure are conceivable.

For further details concerning the device for determining a refractive error of at least one eye of a user, reference may be made to the method device for determining a refractive error of at least one eye of a user as disclosed elsewhere herein.

On a global scale, the occurrence of non-corrective defective vision constitutes the most frequent case for a low or advanced visual impairment. In order to determine the refractive error of at least one eye of a user the method and the device according to the present disclosure exhibit various advantages with respect to the prior art. In particular, the method and the device allow determining values for the spherical and the cylindrical proportions of the refractive error, thereby, using a simple and easy-to-use approach, in particular without requiring at least one of: an optometrist, an ophthalmologist, a set of measuring glasses or a sophisticated apparatus, such as an autorefractive device, designated for this purpose. Consequently, the method and the device provide a powerful tool for determining values for the refractive error which incorporates easy applicability and short test durations. Herein, an implementation of the hardware as well as an incorporation of the software is designed for making the tool applicable even for untrained users or personnel.

Thus, the refractive error of at least one eye of the user can be determined in a fashion which is applicable on a global scale to all kinds of users, including children, elderly or handicapped people, whereby difficulties with communication or compliance can be avoided as far as possible. Furthermore, the present method and device for determining the refractive error is adapted for providing an objective measure, wherein measurements from different performances can easily be stored and compared, thus allowing an assessment of long-term development of the at least one refractive error in at least one eye or the eyes of a user. Further, the present method and device can even be applied at home as a screening tool, potentially implemented even in augmented reality or a mobile communication device. In this fashion, the present disclosure can be used as a screening tool by which the visual impairment can be determined on a regular basis. As a result thereof, stepwise degradation of visual function of a user can be detected earlier and treated much more efficiently.

Summarizing, the exemplary embodiments of the following Clauses are particularly preferred within the scope of the present disclosure:

Clause 1. A method for determining at least one refractive error of at least one eye of a user, the method comprising the following steps:

displaying an image to a user, wherein the image comprises at least one spatial modulation;

optionally recording a reaction of the user to a variation of the spatial modulation over time;

detecting a point in time at which a perception threshold of the user is indicated by a reaction of the user; and determining a value for the at least one refractive error of the at least one eye of the user from the at least one spatial modulation in the image at the point in time, wherein the image comprises a source image having a plurality of picture elements, wherein values for at least one image parameter are assigned to the picture elements, wherein the spatial modulation in the image is generated in a manner that the values of the at least one image parameter of the picture elements determine the values of at least one modulation parameter of the at least one spatial modulation in the image.

Clause 2. The method according to the preceding Clause, wherein the at least one image parameter of the picture elements is selected from: at least one of an intensity, a grayscale, a color, a polarization, or a temporal variation of the picture elements.

Clause 3. The method according to any one of the preceding Clauses, wherein a type of modulation is selected from at least one of: a pulse width modulation, a frequency modulation, an amplitude modulation.

Clause 4. The method according to the preceding Clause, wherein the modulation comprises a carrier frequency, wherein the carrier frequency corresponds to a spatial frequency of the spatial modulation.

Clause 5. The method according to the preceding Clause, wherein a phase of the at least one carrier frequency is, additionally, modulated.

Clause 6. The method according to any one of the two preceding Clauses, wherein the type of modulation is the pulse width modulation, wherein the modulation parameter is a duty cycle within a spatial period, wherein the spatial period corresponds to a reciprocal value of the special frequency.

Clause 7. The method according to the preceding Clause, wherein the duty cycle refers to a portion of the spatial period during which the modulation is applied.

Clause 8. The method according to any one of the four preceding Clauses, wherein the type of modulation is the amplitude modulation, wherein the modulation parameter is an amplitude of the modulation.

Clause 9. The method according to any one of the five preceding Clauses, wherein the type of modulation is the frequency modulation, wherein the modulation parameter is a further frequency superimposed on the modulation.

Clause 10. The method according to any one of the preceding Clauses, wherein the variation of the spatial modulation in the image over time is achieved by varying at least one spatial frequency of the spatial modulation.

Clause 11. The method according to any one of the preceding Clauses, wherein the variation of the spatial modulation in the image over time is achieved by varying a distance between the image and the at least one eye of the user.

Clause 12. The method according to any one of the preceding Clauses, wherein the variation of the spatial modulation in the image over time is achieved by rotating the image in a plane perpendicular with respect to a direction of view of the user.

Clause 13. The method according to the preceding Clause, wherein the rotating of the image in the plane perpendicular with respect to the direction of view of the user is performed after, before, or concurrently with at least one of the varying of the at least one spatial frequency of the spatial modulation or the varying of the distance between the image and the at least one eye of the user.

Clause 14. The method according to any one of the four preceding Clauses, wherein the variation of the spatial modulation time is performed until the perception threshold of the user for the source image as comprised by the image is indicated by the reaction of the user.

Clause 15. The method according to any one of the preceding Clauses, wherein the value for the refractive error of the at least one eye of the user is determined by demodulating the image.

Clause 16. The method according to the preceding Clause, wherein at least one filter is used for demodulating the image.

Clause 17. The method according to the preceding Clause, wherein the at least one filter is selected from: a low pass filter, an optical filter.

Clause 18. The method according to the preceding Clause, wherein the low pass filter is a Gauss filter or a $Sinc^2$ filter.

Clause 19. The method according to any one of the two preceding Clauses, wherein the optical filter is a simulated spectacle lens having a predefined visual correction.

Clause 20. A computer program product comprising executable instructions for performing a method for determining at least one refractive error of at least one eye of a user according to any one of the preceding Clauses.

Clause 21. A method for producing at least one spectacle lens for the at least one eye of the user, wherein the producing of the spectacle lens comprises processing a lens blank, wherein the processing of the lens blank is based on instructions configured to compensate at least one refractive error of the at least one eye of the user, wherein the determining of the refractive error of the at least one eye of the user is performed according to a method for determining the at least one refractive error of the at least one eye of a user according to any one of the preceding Clauses.

Clause 22. A device for determining at least one refractive error of at least one eye of a user, the device comprising
  a screen, wherein the screen unit is configured to display an image and a variation of a spatial modulation in the image to a user;
  optionally an input unit, wherein the input unit is configured to record a reaction of the user to the variation of the spatial modulation in the image over time;
  an evaluation unit, wherein the evaluation unit is configured to detect a point in time at which a perception threshold of the user is indicated by a reaction of the user, and to determine a value for the at least one refractive error of the at least one eye of the user from the at least one spatial modulation in the image at the point in time,
  wherein the image comprises a source image having a plurality of picture elements, wherein values for at least one image parameter are assigned to the picture elements, wherein the evaluation unit is further configured to generate the spatial modulation in the image in a manner that the values of the at least one image parameter of the picture elements determine the values of at least one modulation parameter of the at least one spatial modulation in the image.

Clause 23. The device according to the preceding Clause, wherein the device further comprises a processing unit configured to generate the image and the variation of the spatial modulation in the image.

Clause 24. The device according to any one of the two preceding Clauses referring to the device, wherein the device further comprises a distance meter configured to determine a distance between the image and the at least one eye of the user.

Clause 25. The device according to any one of the three preceding Clauses, wherein the screen is integrated in at least one of: a mobile communication device, a virtual reality headset, smart glasses.

Clause 26. The device according to any one of the four preceding Clauses, wherein at least one of the screen, the input unit, the evaluation unit, the processing unit and the distance meter is comprised by at least one of: the mobile communication device, the virtual really headset.

Clause 27. The device according to any one of the five preceding Clauses, wherein the input unit comprises a keyboard having at least one key configured to be pressed by the user to express the reaction.

Clause 28. The device according to any one of the two preceding Clauses, wherein the mobile communication device is selected from a smartphone or a tablet.

Further optional features and exemplary embodiments of the present disclosure are disclosed in more detail in the subsequent description. Therein, the respective optional features may be realized in an isolated fashion as well as in any arbitrary feasible combination, as the skilled person will realize. It is emphasized here that the scope of the disclosure is not restricted by the exemplary embodiments.

BRIEF DESCRIPTION OF THE DRAWINGS

The disclosure will now be described with reference to the drawings wherein.

DESCRIPTION OF EXEMPLARY EMBODIMENTS

Figure 1:
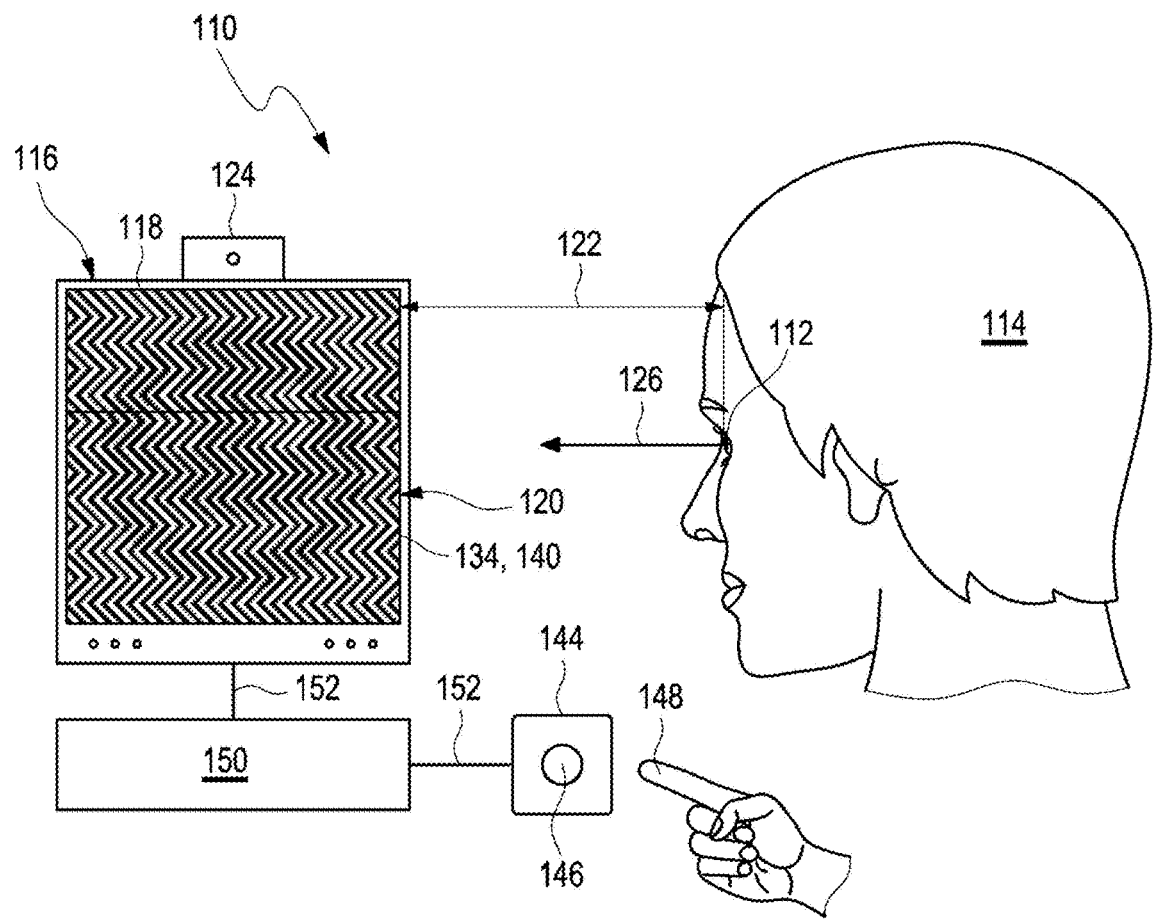
FIG. 1 illustrates an exemplary embodiment of a device for determining a refractive error of at least one eye of a user according to the present disclosure.

FIG. 1 illustrates an exemplary embodiment of a device 110 for determining a refractive error of at least one eye 112 of a user 114. As schematically shown, the exemplary device 110 of FIG. 1 comprises—without limiting the scope of the disclosure—an electronic device 116 having a screen 118 which is configured to display an image 120 to the user 114. Herein, the electronic device 116 can, preferably, be selected from a monitor, a smartphone or a tablet; however further kinds of electronic device 116 may also be feasible. In an alternative embodiment (not depicted here), the image 120 may, as described above, displayed to the user 114, for example by an assistant supporting the user 114, using a cardboard on which the image may be printed. However, further alternatives may also be feasible.

In the exemplary embodiment as shown in FIG. 1, the electronic device 116 which comprises the screen 118 is located at a fixed place, wherein the user 114 may move to alter a distance 122 between the image 120 and the at least one eye 112 of the user 114. As an alternative (not depicted here), the screen 118 may be movable, thus enabling an alteration of the distance 122 between the image 120 and the at least one eye 112 of the user 114. In order to determine a value for the distance 122 between the image 120 and the at least one eye 112 of the user 114, the device 110 can, as further schematically depicted in FIG. 1, comprise a distance meter 124 which is configured to determine the distance 122 between the image 120 and the at least one eye 112 of the user 114.

In addition, the device 110 may be configured to rotate the screen 118 displaying the image 120 within a plane being perpendicular with respect to a direction of view 126 of the user 114. In the exemplary device 110 as illustrated in FIG. 1, rotating the screen is, however, dispensable since a rotation of the image 120 in a plane which is perpendicular to the direction of view 126 of the user 114 can easily be performed by digitally rotating the image 120 on the screen 118. However, the image 120 may, in the alternative embodiment (not depicted here) as described above, be rotated, for example by the assistant, within the plane being perpendicular to the direction of view 126 of the user 114 by turning the cardboard in a respective fashion, whereby the distance 122 between the cardboard and the at least one eye 112 of the user 114 is maintained. However, further ways of rotating the image 120 may also be conceivable.

Figure 3A:
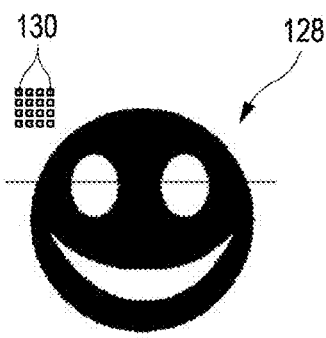
FIGS. 3A to 3D illustrate various kinds of images as used in the method for determining a refractive error of at least one eye of a user according to the present disclosure.

As further illustrated in FIGS. 1 and 3A, the image 120 comprises a source image 128 having a plurality of picture elements 130 which are schematically indicated in FIG. 3A by various selected portions of the source image 128 that can be individually addressed. The source image 128 as used herein constitutes a schematic drawing of a simple logo which only comprises sections in black and white as further depicted in FIG. 3A. However, further kinds of other simple logos, animal, toys, natural objects such as a house or a fruit, could also be used for this purpose. Accordingly, a value of "black" or of "white" can be assigned to each picture element 130 of the source image 128, depending on whether the picture element 130 is predominantly located in the black section or in the white section of the drawing, respectively. With regard to the present disclosure, an image parameter which may be denoted by the term "shade" can be used, wherein a value for the image parameter "shade" is assigned to the picture element 130. In the exemplary embodiment of FIG. 3A, the image parameter "shade" of each picture element 130 of the source image 128 can, thus, either assume the value of "black" or the value of "white."

Figure 3B:
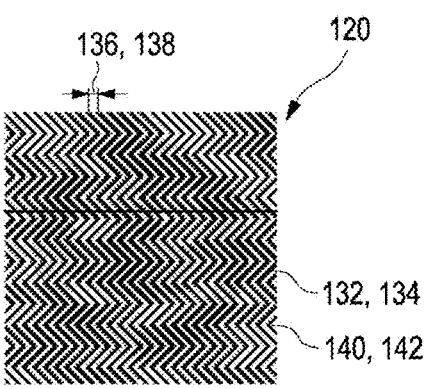
Figure 4B:
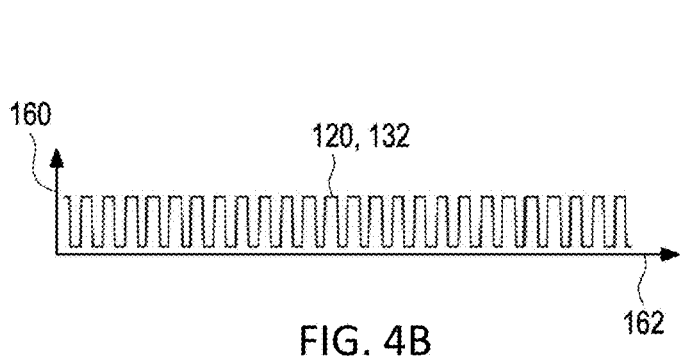

As shown in FIGS. 1 and 3B, the image 120 comprises a spatial modulation 132 in form of alternating black and white stripes 134, wherein the spatial modulation 132 is generated by individually modulating the picture elements 130. As depicted there, the spatial modulation 132 comprises a spatial frequency which is, usually, defined, as a reciprocal value of a spatial distance 136 which reflects a spatial period 138 of repetition of a pattern within the image 120. For a purpose of generating the spatial modulation 132, the value of the at least one image parameter of the picture element 130 determines, in accordance with the present disclosure, a value for at least one modulation parameter of the at least one spatial modulation 132 of the picture element 130. In the exemplary embodiment of FIGS. 1, 3A, and 3B, the value of the image parameter "shade" of the picture element 130 as described above is, thus, used for determining the value of the at least one modulation parameter of the at least one spatial modulation 132 of the picture element 130.

The spatial modulation 132 used for generating the image 120 as depicted in FIGS. 1 and 3B, is a pulse width modulation, which refers to a type of modulation that comprises a carrier frequency which is modulated by a so-called "duty cycle" within each spatial period 138. Thus, the duty cycle acts as the modulation parameter as indicated above while the spatial frequency in the image 120 corresponds to the carrier frequency of the pulse width modulation. As defined above, the "duty cycle" refers to a portion of a particular spatial period 138 during which the modulation is applied, which can be described in this particular example by the width of the alternating black and white stripes 134. In the embodiment of FIGS. 1 and 3B, the value of the modulation parameter within each spatial period 138 corresponds to the value for the duty cycle within each spatial period 138, wherein either a value of approx. "0.6" or of approx. "0.4" can be assigned to each picture element 130. As illustrated there, the value of "0.6" results in thick black stripes 134 in the image 120 while the value of "0.4" results in thick black stripes 134 in the image 120, whereby the value of the spatial period 138 which corresponds to the carrier frequency of the pulse width modulation remains constant all over the image 120.

According to the present disclosure, the value for the image parameter "shade" of the picture elements 130 within the spatial period 138, thus, determines whether the value of "0.6" or of "0.4" is used for the duty cycle within the spatial period 138. Therefore, the duty cycle assumes the value of "0.6" in the black sections of the source image 128, while the duty cycle assumes the value of "0.4" in the white sections of the source image 128. As a result, the image 120 has, on one hand, first areas comprising the black sections of the source image 128 and the thick black stripes 134 having the value of "0.6" for the duty cycle and, on the other hand, second areas comprising the white sections of the source image 128 and the thin black stripes 134 having the value of "0.4" for the duty cycle. Thus, the value of the duty cycle may vary between adjacent spatial periods 138, whereby the length of the spatial period 138 is, however, left unaffected.

In addition, the image 120 as illustrated in FIGS. 1 and 3B comprises a zig-zag pattern 140 which is generated by, additionally, modulating a phase of the spatial frequency perpendicular to the alternating black and white stripes 134 in a sinusoidal fashion. As a result thereof, an inclination of the alternating black and white stripes 134 varies between adjacent rows 142 in an alternating fashion as shown in FIGS. 1 and 3B between a leftward direction and a rightward direction. However, various other examples may be conceivable for the modulation in the image 120.

Alternatively or in addition, at least one other modulation type (not depicted here) can be used for the at least one spatial modulation 132, wherein the other modulation type may, particularly, be selected from an amplitude modulation or a frequency modulation. Using the amplitude modulation, on one hand, would, as further depicted in FIGS. 4A to 4D, result in a variation of the intensity of the alternating black and white stripes 134 depending on the value for the image parameter "shade" of the picture elements 130 within the spatial period 138, whereby the width of the alternating black and white stripes 134 and the length of the spatial period 138 would remain constant. Using the frequency modulation, on the other hand, would result in a variation of a number of alternating black and white stripes 134 within the spatial period 138, again depending on the value for the image parameter "shade" of the picture elements 130 within the spatial period 138, whereby the length of the spatial period 138 would, again, remain constant. Further examples are feasible.

As further illustrated in FIG. 1, the device 110 for determining the refractive error of the at least one eye 112 of a user 114 comprises an input unit 144, wherein the input unit 144 is configured to record a reaction of the user 114 to the variation of the spatial modulation 132 in the image 120 over time. For a purpose of varying the spatial modulation 132 in the image 120 over time, at least one of the following embodiments may be selected:
varying the spatial frequency of the spatial modulation 132;
varying the distance 122 between the image 120 and the at least one eye 112 of the user 114; and
rotating the image 120 in a plane perpendicular with respect to the direction of view 126 of the user 114.

As indicated above, the spatial frequency of the spatial modulation 132 may be varied, either in a direct fashion according to embodiment (i), by displaying a different image 120 having a different a spatial frequency to the user 114 or, in an indirect fashion according to embodiment (ii), by varying the distance 122 between the image 120 and the at least one eye 112 of the user 114. As further indicated above, the image 120 may be rotated in a plane being perpendicular to the direction of view 126 of the user 114 according to embodiment (iii) by using a rotating unit configured to physically rotate the image 120. However, the image 120 may also be rotated in a plane that is perpendicular to the direction of view 126 of the user 114 in a virtual fashion by rotating the image 120 as displayed on the screen 118. In addition, further ways of rotating the image 120 may also be conceivable.

As depicted in FIG. 1, the input unit 144 may comprise a keyboard 146 having one or more buttons which can be pressed by a finger 148 of the user 114 in order to indicate the desired reaction of the user 114. However, further kinds of input units 144 may also be feasible, such as one or more microphones (not depicted here) configured to receive a sound produced by the user 114 to indicate the desired reaction. As a further alternative or in addition, the reaction of the user 114 can be recorded using a measuring device, such as a video camera (not depicted here) configured to record a video of the user 114, wherein the reaction of the user 114 can be observed by displaying the video or, alternatively or in addition, by image processing. As a further alternative or in addition, the measuring device can be or comprise an eye tracker configured to monitor eye movements of the user 114, preferably selected from pursuit eye movements of the eyes 112 of the user 114.

As further illustrated in FIG. 1, the device 110 comprises an evaluation unit 150, which can be connected to at least one of the screen 118, the distance meter 124 and the input unit 144, in a wireless fashion, for example using a Bluetooth connection (not depicted here), or in a wire-bound fashion by using one or more direct connections 152, for example one or more USB connections. Herein, the evaluation unit 150 may be or comprise a processing unit (not depicted here), wherein the processing unit may be configured to generate the image 120 and the variation of the spatial modulation 132 in the image 120.

In accordance with the present disclosure, the evaluation unit is configured to detect a point in time at which a perception threshold of the image 120 for the user 114 is indicated by the reaction of the user 114 to the image 120, in particular to the variation of the spatial modulation 132 in the image 120 over time. As defined above, the perception threshold may refer to a first event, in which the user may be able to recognize the source image 128 within the image 120, or to a further event, in which the user can just still recognize the source image 128 before the source image 128 vanishes from the image 120 as recognized by the user 114.

Accordingly, the perception threshold can be used to determine the point in time at which the first event or the further event may occur. However, by knowing the point in time as deduced in this fashion, respective values can be derived for the at least one modulation parameter of the spatial modulation 132 in the image 120 at the point in time, on one hand, and, due to the relationship between the modulation parameter used for generating the spatial modulation 132 in the image 120 and the at least one image parameter initiating the spatial modulation 132 in the image 120, for the at least one image parameter at the point in time, on the other hand. In accordance with the present disclosure, such a deduction can be used to determine a value for the at least one refractive error of the at least one eye 112 of the user 114. The value for the at least one refractive error of the at least one eye 112 of the user 114 can, subsequently, be reported to at least one of the user 114 or the assistant, preferably, via the screen 118 after the end of displaying the one or more images 120 to the user 114. However, further fashions for reporting the value of the at least one refractive error of the at least one eye 112 of the user 114 are conceivable.

In particular, by varying the spatial frequency of the spatial modulation 132, either according to embodiment (i) or to embodiment (ii), without rotating the image 120 according to embodiment (iii) as defined above, a refractive value of a single main section of a spherocylindrical lens which may be required to correct this part of the refractive error of the user 114 can, thus, be determined, on one hand. On the other hand, rotating the image 120 according to embodiment (iii) allows determining a cylindrical power which refers, as defined above, to an algebraic difference between the refractive values of the main sections and the cylinder axis that indicates the direction of the main section of the spectacle lens whose apex refractive index is used as reference.

In a particularly preferred embodiment, the desired value for the refractive error of the at least one eye of the user 114 can be determined by demodulating the image which has, previously, been modulated by the at least one type of modulation using the at least one modulation parameter. Herein, a demodulation of the image 120 can be considered as filtering the image at the point in time, whereby a filter which can be used for the demodulation of the image 10 may, thus, comprise additional information related to the point in time. In particular, a frequency which is used for modulating the source image 128 can be considered as proportional to a power of the filter which is, thus, proportional to the desired value for the refractive error of the user 114.

Figure 3C:
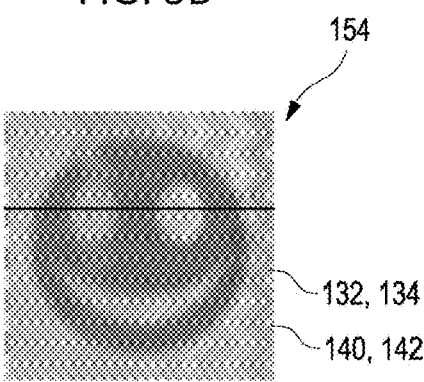

As already described above, the filter as used for the demodulation, typically, comprises a low pass filter, in particular the two-dimensional equivalent of the low pass filter which is, usually, denoted by the terms "Gauss filter" or "Since filter," which is configured to remove high frequency portions from the image 120. As schematically depicted in FIG. 3C, the filter may be capable of at least partially removing the spatial modulation 132 from the image 120, whereby the source image 128 can be reconstructed to a large extent as denoted by the reference sign 154. while the spatial modulation 132 comprising the black and white stripes 134 is still be visible to a considerable extent. In order to be able to determine the cylindrical power and the cylinder axis as defined above, more than one filter can be used for different axes of the image.

Figure 3D:
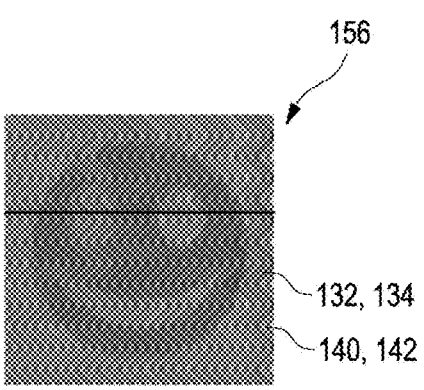

Alternatively or in addition, an optical filter may be used for the same purpose with similar efficiency as illustrated in FIG. 3D. As indicated above, an optical filter refers to a simulated spectacle lens having a predefined visual correction, such as indicated in ±diopters. Herein, a series of different optical filters, wherein each optical filter corresponds to a simulated different spectacle lens having a different value for the visual correction, can be is superimposed, in particular by using the evaluation device 150, onto the image 120 in order to produce a corrected image. The result of applying an exemplary optical filter having +1.0 diopter is schematically depicted in FIG. 3D which shows a further reconstruction 156 of the source image 128 while the spatial modulation 132 comprising the black and white stripes 134 is also here still be visible to a considerable extent.

Figure 4A:
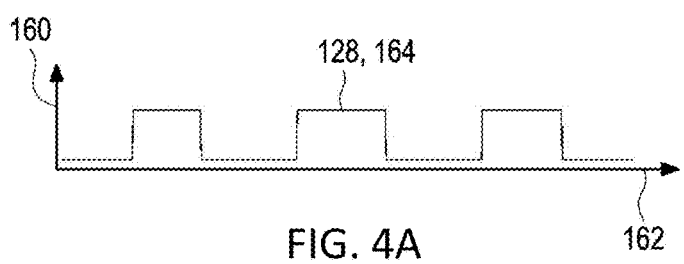
FIGS. 4A to 4D illustrate variations of grayscale values which correspond to the images as shown in FIGS. 3A to 3D.
Figure 4C:
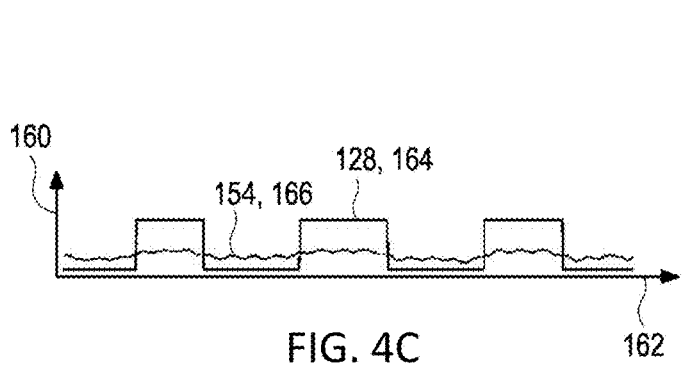
Figure 4D:
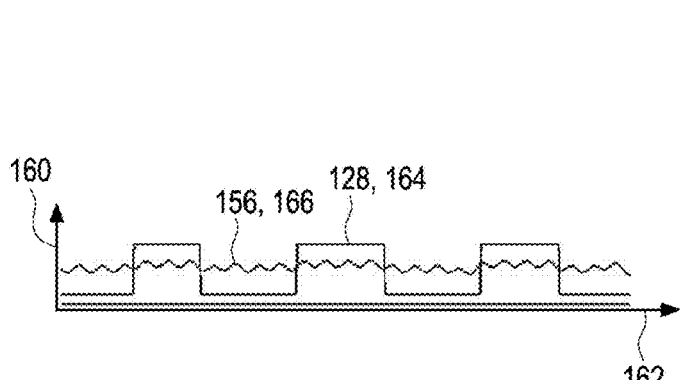

Corresponding to each of FIGS. 3A to 3D, FIGS. 4A to 4D schematically illustrate a respective grayscale values 160. For this purpose, in each of FIGS. 4A to 4D, the horizontal axis refers to a location 162 while the vertical axis refers to the grayscale value 160 at the corresponding location 162. Herein, FIG. 4A illustrates a course 164 of the grayscale values 160 over black and white areas of the source image 128. Further, FIG. 4B displays the image 120 comprising the spatial modulation 132 of the grayscale values 160. Further, FIGS. 4C and 4D illustrate the course 164 of the grayscale values 160 over the source image 128 and the resulting demodulated course 166 of the variation of the grayscale values 160.

Figure 2:
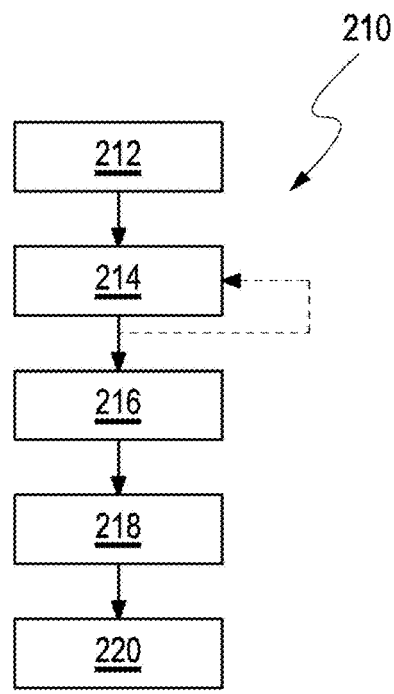
FIG. 2 illustrates an exemplary embodiment of a method for determining a refractive error of at least one eye of a user according to the present disclosure.

FIG. 2 schematically illustrates an exemplary embodiment of a method 210 for determining a refractive error of at least one eye 112 of a user 114 according to the present disclosure.

In a displaying step 212 according to step a), the image 120 is displayed to the user 114, wherein the image 120 comprises the at least one spatial modulation 132 as described above in more detail.

In a recording step 214 according to step b), the reaction of the user 114 to the variation of the spatial modulation 132 in the image 120 may be recorded over time. Herein, the spatial modulation 132 in the image 120 can be varied, preferably by using at least one of the embodiments (i) to (iii) as indicated above in more detail. Herein, the recording step 214 may be repeated with different images 120 displaying at least one of a different value of the spatial modulation 132 or a different orientation of the spatial modulation 132 in a plane perpendicular to the direction of view 126 of the user 114 until the point in time is detected in a detecting step 216.

In the detecting step 216 according to step c), the point in time is detected at which the perception threshold of the user 114 is indicated by a reaction of the user 114 to the particular image 120 as currently displayed to the user 114. For this purpose, the input unit 144 as described above in more detail may be used, however, further kinds of input units may also be feasible. In an alternative embodiment, the perception threshold of the user 114 may be indicated by a reaction of the user 114 without requiring an input unit, wherein the reaction of the user 114 may, preferably, be at least one physiological reaction, in particular, selected from at least one of the physiological reactions as described above in more detail. In this alternative embodiment, performing the recording step 214 according to step b) may be dispensable.

In a determining step 218 according to step d), the value of at least one modulation parameter of the at least one spatial modulation 132 in the image 120 at the point in time as detected in the detecting step 216 is used for determining a desired value 220 for the at least one refractive error of the at least one eye 112 of the user 114. For details concerning the determining step 218, reference can be made to the description above.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

LIST OF REFERENCE SIGNS 110 device
112 eyes
114 user
116 electronic device 118 screen
120 image
122 distance
124 distance meter
126 direction of view
128 source image
130 picture element
132 spatial modulation
134 stripes
136 spatial distance
138 spatial period
140 zig-zag pattern
142 row
144 input unit
146 keyboard
148 finger
150 evaluation unit
152 connection
154 reconstructed source image
156 reconstructed source image
160 grayscale value
162 location
164 course
166 course
210 method
212 displaying step
214 recording step
216 detecting step
218 determining step
220 value for the refractive error

The invention claimed is:

1. A method for determining at least one refractive error of at least one eye of a user, the method comprising the following steps:
displaying a source image to a user, the source image having a plurality of picture elements and being recognizable by the user;
inquiring whether the user recognizes the source image;
displaying at least one image to the user on a screen, wherein the at least one image contains at least one spatial modulation;
detecting a point in time at which a perception threshold of the user is indicated by a reaction of the user using an evaluation unit; and
determining a value for the at least one refractive error of the at least one eye of the user from the at least one spatial modulation in the at least one image at the point in time using the evaluation unit,
wherein the at least one image contains the source image, wherein values for at least one image parameter are assigned to the plurality of picture elements, and wherein the at least one spatial modulation in the at least one image is generated in a manner that the values of the at least one image parameter of the plurality of picture elements determine the values of at least one modulation parameter of the at least one spatial modulation in the at least one image.

2. The method according to claim 1, further comprising the following step:
recording the reaction of the user to at least one variation of the at least one spatial modulation over time using an input unit.

3. The method according to claim 2, wherein the variation of the at least one spatial modulation time is performed until the perception threshold of the user for the source image as comprised by the at least one image is indicated by the reaction of the user.

4. The method according to claim 2, wherein the at least one variation of the at least one spatial modulation in the at least one image over time is selected from at least one of:
(i) varying at least one spatial frequency of the at least one spatial modulation;
(ii) varying a distance between the at least one image and the at least one eye of the user; and
(iii) rotating the at least one image in a plane perpendicular with respect to a direction of view of the user.

5. The method according to claim 4, wherein the rotating of the at least one image in the plane being perpendicular with respect to the direction of view of the user is performed after, before, or concurrently with at least one of the varying of the at least one spatial frequency of the at least one spatial modulation or the varying of the distance between the at least one image and the at least one eye of the user.

6. The method according to claim 1, wherein the at least one image parameter of the picture elements is selected from at least one of an intensity, a grayscale, a color, a polarization, or a temporal variation of the picture elements.

7. The method according to claim 1, wherein the perception threshold is selected from at least one of a contrast threshold, a color threshold, a polarization threshold, or a temporal threshold.

8. The method according to claim 1, wherein a type of the at least one spatial modulation is selected from at least one of a pulse width modulation, a frequency modulation, an amplitude modulation.

9. The method according to claim 1, wherein the at least one spatial modulation comprises at least one spatial frequency, and wherein the at least one spatial frequency corresponds to at least one carrier frequency of the modulation.

10. The method according to claim 9, wherein a phase of the at least one carrier frequency is, additionally, modulated.

11. The method according to claim 1, wherein the value for the refractive error of the at least one eye of the user is determined by demodulating the at least one image.

12. The method according to claim 11, wherein at least one filter is used for demodulating the at least one image.

13. A computer-readable non-transitory storage medium carrying a computer program comprising instructions which, when executed by a computer, cause the computer to carry out the method of claim 1 by using at least one computer program.

14. A computer program stored on a non-transitory storage medium and having executable instructions for performing a method for determining a refractive error of at least one eye of a user, the method comprising:
displaying a source image to a user, the source image having a plurality of picture elements and being recognizable by the user;
inquiring whether the user recognizes the source image;
displaying at least one image to the user on a screen, wherein the at least one image contains at least one spatial modulation;
detecting a point in time at which a perception threshold of the user is indicated by a reaction of the user using an evaluation unit; and
determining a value for the at least one refractive error of the at least one eye of the user from the at least one spatial modulation in the at least one image at the point in time using the evaluation unit,
wherein the at least one image contains the source image, h, wherein values for at least one image parameter are assigned to the plurality of picture elements, and wherein the at least one spatial modulation in the at least one image is generated in a manner that the values of the at least one image parameter of the plurality of picture elements determine the values of at least one modulation parameter of the at least one spatial modulation in the at least one image.

15. The computer program according to claim 14, wherein the method further comprises the following step:
recording the reaction of the user to at least one variation of the at least one spatial modulation over time using an input unit.

16. The computer program according to claim 15, wherein the variation of the at least one spatial modulation time is performed until the perception threshold of the user for the source image as comprised by the at least one image is indicated by the reaction of the user.

17. The computer program according to claim 15, wherein the at least one variation of the at least one spatial modulation in the at least one image over time is selected from at least one of:
(i) varying at least one spatial frequency of the at least one spatial modulation;
(ii) varying a distance between the at least one image and the at least one eye of the user; and
(iii) rotating the at least one image in a plane perpendicular with respect to a direction of view of the user.

18. The computer program according to claim 17, wherein the rotating of the at least one image in the plane being perpendicular with respect to the direction of view of the user is performed after, before, or concurrently with at least one of the varying of the at least one spatial frequency of the at least one spatial modulation or the varying of the distance between the at least one image and the at least one eye of the user.

19. The computer program according to claim 14, wherein the at least one image parameter of the picture elements is selected from at least one of an intensity, a grayscale, a color, a polarization, or a temporal variation of the picture elements.

20. The computer program according to claim 14, wherein the perception threshold is selected from at least one of a contrast threshold, a color threshold, a polarization threshold, or a temporal threshold.

21. The computer program according to claim 14, wherein a type of the at least one spatial modulation is selected from at least one of a pulse width modulation, a frequency modulation, an amplitude modulation.

22. The computer program according to claim 14, wherein the at least one spatial modulation comprises at least one spatial frequency, wherein the at least one spatial frequency corresponds to at least one carrier frequency of the modulation.

23. The computer program according to claim 22, wherein a phase of the at least one carrier frequency is, additionally, modulated.

24. The computer program according to claim 14, wherein the value for the refractive error of the at least one eye of the user is determined by demodulating the at least one image.

25. The computer program according to claim 24, wherein at least one filter is used for demodulating the at least one image.

26. A method for producing at least one spectacle lens for the at least one eye of the user, wherein the producing of the spectacle lens comprises
processing a lens blank, wherein the processing of the lens blank is based on instructions configured to compensate at least one refractive error of the at least one eye of the user; and
determining of the refractive error of the at least one eye of the user by performing the following steps:
displaying a source image to a user, the source image having a plurality of picture elements and being recognizable by the user;
inquiring whether the user recognizes the source image;
displaying at least one image to the user on a screen, wherein the at least one image comprises at least one spatial modulation;
detecting a point in time at which a perception threshold of the user is indicated by a reaction of the user using an evaluation unit; and
determining a value for the at least one refractive error of the at least one eye of the user from the at least one spatial modulation in the at least one image at the point in time using the evaluation unit,
wherein the at least one image contains the source image, wherein values for at least one image parameter are assigned to the plurality of picture elements, and wherein the at least one spatial modulation in the at least one image is generated in a manner that the values of the at least one image parameter of the plurality of picture elements determine the values of at least one modulation parameter of the at least one spatial modulation in the at least one image.

27. The method according to claim 26, wherein the determining of the refractive error of the at least one eye of the user further comprises the following step:
recording the reaction of the user to at least one variation of the at least one spatial modulation over time using an input unit.

* * * * *

UNITED STATES PATENT AND TRADEMARK OFFICE
CERTIFICATE OF CORRECTION

| | |
|---|---|
| PATENT NO. | : 12,016,627 B2 |
| APPLICATION NO. | : 18/398286 |
| DATED | : June 25, 2024 |
| INVENTOR(S) | : Alexander Leube et al. |

Page 1 of 1

It is certified that error appears in the above-identified patent and that said Letters Patent is hereby corrected as shown below:

In the Specification

In Column 7, Line 57: change "l/m" to -- 1/m --

In Column 23, Line 31: change "Since" to -- $Sinc^2$ --

In the Claims

In Column 26, Line 27, Claim 8: change "an" to -- or an --

In Column 26, Lines 64 to 65, Claim 14: change "image h," to -- image, --

In Column 27, Line 46, Claim 21: change "an" to -- or an --

Signed and Sealed this
Twenty-ninth Day of October, 2024

Katherine Kelly Vidal
*Director of the United States Patent and Trademark Office*